United States Patent
Garcia et al.

[11] Patent Number: 5,923,771
[45] Date of Patent: Jul. 13, 1999

[54] SENSOR DEVICE FOR COUNTING AND DETERMINING SURFACE BUBBLE AND CRACK SIZES IN COPPER BARS DURING CONTINUOUS TAPPING

[75] Inventors: Daniel Cardenas Garcia; Daniel Aguilera Longoria; Fernado Luengas Ruiz, all of Querétaro, Mexico

[73] Assignee: Servicios Condumex S.A. De C.V. Carretera ASLP. KM., Queretero, Mexico

[21] Appl. No.: 08/791,242

[22] Filed: Jan. 30, 1997

[30] Foreign Application Priority Data

Aug. 21, 1996 [MX] Mexico ............................... 963554

[51] Int. Cl.⁶ ................................................ G06K 9/00
[52] U.S. Cl. ........................ 382/141; 348/92; 348/128; 348/131; 148/282
[58] Field of Search ......................... 382/141, 108, 382/286; 428/544; 348/86, 92, 128, 131; 266/100; 148/508, 282

[56] References Cited

U.S. PATENT DOCUMENTS

| | | | |
|---|---|---|---|
| 4,118,732 | 10/1978 | Ichijima et al. | 348/132 |
| 4,219,844 | 8/1980 | Ohsumi et al. | 348/131 |
| 5,392,359 | 2/1995 | Futamura et al. | 382/141 |
| 5,406,104 | 4/1995 | Gorria et al. | 382/141 |
| 5,440,648 | 8/1995 | Roberts et al. | 382/141 |
| 5,537,669 | 7/1996 | Evans et al. | 382/141 |
| 5,539,656 | 7/1996 | Annigeri et al. | 382/141 |
| 5,680,473 | 10/1997 | Kanzaka et al. | 382/141 |

*Primary Examiner*—Joseph Mancuso
*Assistant Examiner*—Gilberto Frederick, II
*Attorney, Agent, or Firm*—Carmen Pili Curtis

[57] ABSTRACT

The present invention relates to a device that measures and counts near surface bubbles on a copper bar, as well as the cracks on the lateral sides. The device detects said flaws in real time. The device is based on the image digitalization technique. The device consists of a personal computer, a video camera, a digitalization card, water and air sprinklers, external monitor and camera frame. The input of the images is performed with the video camera protected within the frame. The object of the water and air sprinklers is to make the bar flaws more visible. The external monitor allows to focus the area of interest and the digitalizing card within the computer, following the instructions of the program, performs the image analysis.

20 Claims, 2 Drawing Sheets

SENSOR DEVICE FOR COUNTING AND DETERMINING SURFACE BUBBLE AND CRACK SIZES IN COPPER BARS DURING CONTINUOUS TAPPING

BACKGROUND OF THE INVENTION

The normal process for producing copper wire rod is to obtain first a rectangular cross section bar, the cross area of which is reduced by means of rolls. The rolls are in above-below and lateral alternate pair systems. By passing through each pair system, the rod area is reduced in a predetermined percentage and this is called reduction step.

During the process of manufacturing copper wire rod from a bar, the flaws that appear in said bar can worsen in each reduction step. Generally, these flaws appear in continuous form, normally said flaws are detected when they cause problems in subsequent processes (such as wire stretching) causing economic losses.

Because of the high demand for wire rod, the manufacturers have tried to monitor the flaws of the bar in real time in order to take corrective actions. However, in the case of bubbles and cracks the normal inspection procedure is to take bar samples with the consequent stoppage of the production process. This is because there is no device that can examine said flaws in real time in a line process.

The analysis of the laboratory samples suggests the modification of operating conditions, but it is not possible to correlate the new operating conditions to the increase or decrease of the bubble and crack number without stopping again the manufacturing process.

To solve this problem inspection devices based on CCD linear elements have been developed. The main problem with this type of devices is the difficulty to synchronize the input of images with the speed of the bar. Besides, it is impossible to use a monitor to observe the zone of the bar which is being examined and the existence of flaws.

With regard to the mentioned above points, the applicant has developed a device to measure and count said flaws in real time. The device which is the object of the present invention has the capacity to count and measure the bubbles that are located near the upper surface of the bar during the wire rod production process. Besides, said device counts the cracks that are generated on the side of the bar during the reduction step in the zones where the largest percentage area reduction is performed, through one or more video cameras.

It is thus an object of the present invention to offer a sensor device to count and determine the size of cracks and bubbles in copper bars during tapping, said device can detect said cracks and bubbles without the need to stop the tapping process.

A further object of the present invention is to offer a novel and reliable method of rapid and precise detection which is easy to handle and without economic losses.

Figure 1:
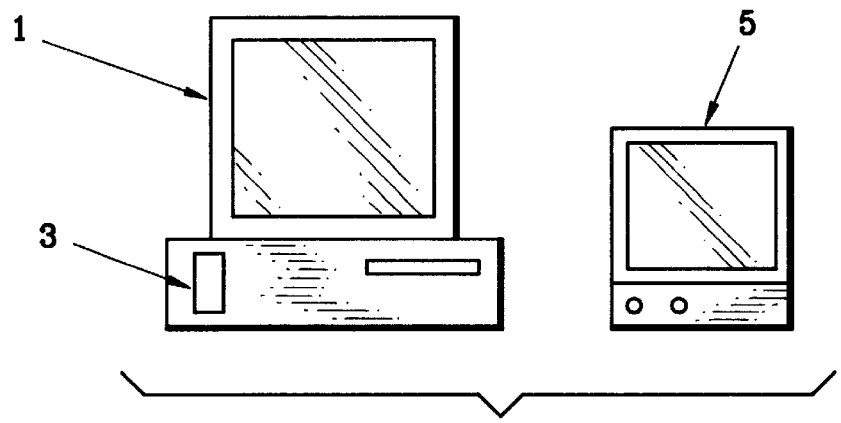
FIG. 1 corresponds to a schematic diagram of the electronic equipments that constitute the sensor device arranged to count and determine the size of cracks and bubbles formed in copper bars.
Figure 2:
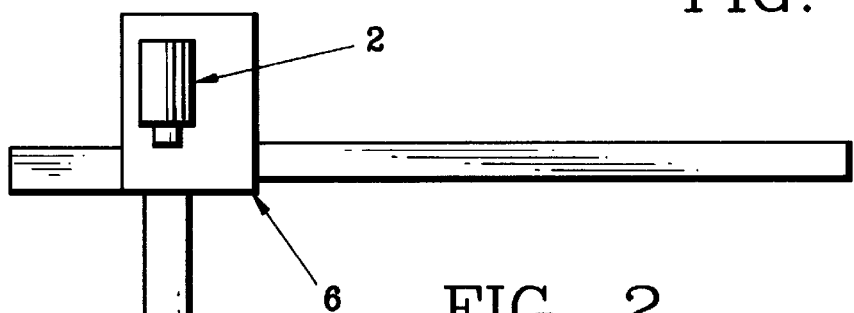
FIG. 2 corresponds to a schematic view of the arrangement of a video camera.
Figure 3:
FIG. 3 corresponds to a schematic view of the arrangement of the video camera and sprinkling elements located before a sample bar.
Figure 4:
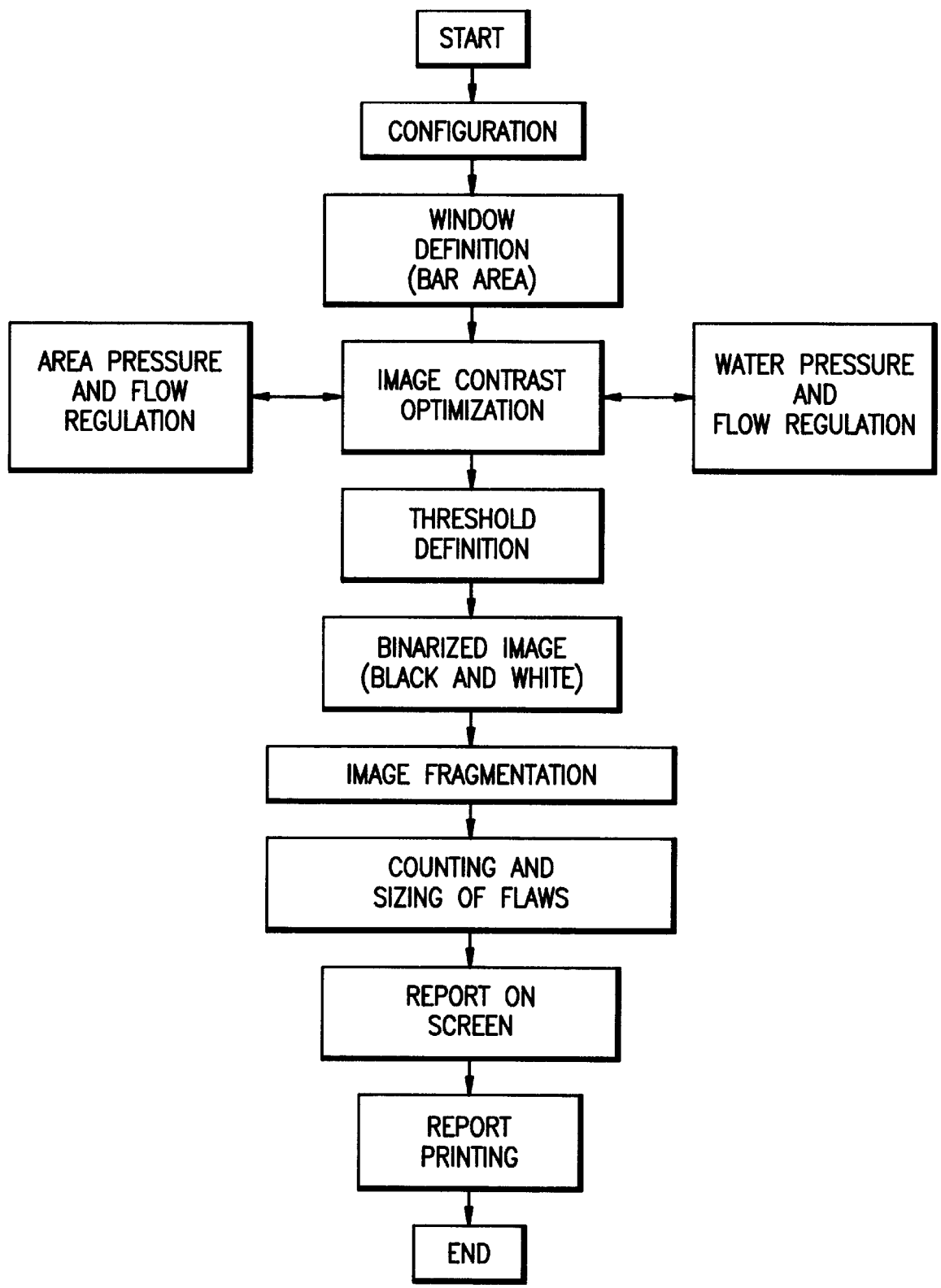
FIG. 4 corresponds to a flow chart of the counting and size determination system.

Hereinbelow the invention will be described according to the drawings of the FIGS. 1 to 4 in order to better explain said invention but without limiting its scope.

DESCRIPTION OF THE INVENTION

The sensor device to count and determine the size of cracks and bubbles in copper bars, FIGS. 1 to 4, is based on the image digitalization technique. Said device is integrated by an intertwined system of electronic components according to the following elements: a personal computer (1) to electronically detect, count and size; wherein said computer must be designed to carry out processing services in real time; a video camera (image input channel) (2) to input the images and which is protected within the frame (6). The video camera used has a CCD sensitive element. Because the object to be visualized is a copper bar at high temperature and in order to avoid the saturation of the camera by the bar luminosity, a density filter is located in front of the lens to lower the intensity of the light that reaches the CCD. It also has a digitalizing card (3), the object of which is to perform the image processing in real time. Said card is located within the computer (1) and analyzes the image according to the instructions given by the program. It also has sprinklers (4) to sprinkle water and air onto the copper bar (7). The water sprinkler throws a jet that cools the copper bar surface and the bubbles that are at a lower temperature than the rest of the bar are visible. In order to avoid the presence of water in the field of vision of the camera, a pressurized air sprinkler is arranged. In this way it is insured that the bubbles are visible and can be analyzed. It also has an external monitor (5) which is used to observe and to focus directly the image of interest coming from the video camera (2). Said monitor is also used to observe the already processed image to fix the input window. It also has a camera frame (6) to protect the camera and its power supply that are located within a metal housing with a window in the front part and with video and power supply connections in the rear part. The housing is mounted on a support at a distance of about 2 meters from the copper bar and has two degrees of freedom (lateral movement and inclination) to allow the camera to offer a better image. In the front part of the housing there is a pipe, the object of which is to avoid that vapors and splatters obstruct the field of vision of the camera.

Procedure to Count and Determine the Size of Cracks and Bubbles

Hereinbelow the method to count and determine the size of cracks and bubbles will be described.

A non-contact device which measures and counts in real time the surface and near surface flaws on a contrasted surface is presented.

The image digitalization technique has evolved towards the recognition of complex patterns that allow the development of algorithms to distinguish objects on a surface. Several techniques that facilitate the image analysis using two different strategies have been developed. The first one involves the analysis of the image as it is normally presented and thus the algorithm complexity increases, as well as the processing time. The second strategy involves the modification in some way of the image to facilitate the analysis. In general terms, in order to obtain a real time processing, even with the progress in computer speed, the second strategy is followed.

The invention consists in the creation of a non-contact device based on image digitalization, which measures and counts in real time the surface flaws on a contrasted surface. In order to reach this objective, first the area to be analyzed is delimited. This involves the establishment of a relation between the sizes of the physical area and the image to be analyzed in the computer. Then, the contrast between the figure (the flaws) and the background is optimized. In our case, this is reached through the establishment of a temperature difference between the vapor caught in the bubbles and the bar metal through a water jet. To avoid that the water splatters the analysis area, a pressurized air sprinkler is used. The water pressure and volume of flow are regulated to obtain a contrasted image that can be watched on the auxiliary monitor with the naked eye. Once the contrasted image is obtained, the device performs the following functions:

It defines a threshold from which the flaws appear in black and the rest of the bar in white.

The image is fragmented in a 640×480 square matrix to which the corresponding size is assigned as representation of the physical object, and the device identifies the color of each square (white if it corresponds to the background or black if it corresponds to a flaw).

Finally, the device, with the position, color and size information for each square, counts and determines the size of the flaws.

For registration purposes, the total of the flaws are grouped in different size categories that can be defined by the user. The information regarding the date and time of the measurement is indicated.

Although this device has been developed for bubbles and cracks counting and size determination in a copper bar, the principle can be used to count and determine the size, in real time, of any type of objects on a contrasted background. This is very useful in the automatization of the industry because the objects to be counted and sized can be: flaws in metals, ceramics and materials in general, fruit, vegetables, sausages, pieces, equipments, etc. Additionally, because of its non contact nature, there is no problem with regard to the alteration or contamination of the object being measured. With appropriate lenses it is even possible to measure objects that are at a large distance as well as microscopic objects.

The above described invention is considered a novelty and its scope is limited only by the following claims.

We claim:

1. A sensor device to count and determine the size of surface cracks and bubbles in copper bar during continuous tapping process comprising:
  a) at least one video camera for producing images of the copper bar;
  b) a personal computer electronically connected to said video camera;
  c) a monitor for directly displaying and focusing the image produced by the at least one video camera;
  d) a housing for fixing and protecting said video camera; and
  e) a means for sprinkling low pressure water and air towards the copper bar; said copper bar being cooled on the outer surface area.

2. The sensor device to count and determine the size of surface cracks and bubbles in copper bar, according to claim 1, wherein the video camera further comprises a CCD sensitive element.

3. The sensor device to count and determine the size of surface cracks and bubbles in copper bar, according to claim 2, wherein the video camera further comprises a density filter in front of the lens for lowering the intensity of the light that reaches the CCD, coming from the luminosity of the copper bar when said bar is at a high temperature of about 1000° C.

4. The sensor device to count and determine the size of surface cracks and bubbles in copper bar, according to claim 1, wherein said personal computer further comprises a digitalizing card for processing the images in real time.

5. The sensor device to count and determine the size of surface cracks and bubbles in copper bar, according to claim 1, wherein the means for water sprinkling directs the water jet towards the copper bar in order to cool the surface of said copper bar or make visible the cracks or bubbles that appear when the temperature decreases compared to the rest of the bar surface.

6. The sensor device to count and determine the size of surface cracks and bubbles in copper bar, according to claim 5, wherein the means for water sprinkling further comprises a pressurized air for removing at a distance the water drops and for insuring a video camera field of vision free from water.

7. The sensor device to count and determine the size of surface cracks and bubbles in copper bar, according to claim 1 wherein the housing further comprises a rear part and a front part.

8. The sensor device to count and determine the size of surface cracks and bubbles in copper bar, according to claim 7 wherein the front part comprises a window.

9. The sensor device to count and determine the size of surface cracks and bubbles in copper bar, according to claim 7 wherein the front part comprises a pipe to avoid vapors and splatters obstructing the video camera field of vision.

10. The sensor device to count and determine the size of surface cracks and bubbles in copper bar, according to claim 7 wherein the rear part comprises the video and a power supply connection.

11. The sensor device to count and determine the size of surface cracks and bubbles in copper bar, according to claim 1, wherein the housing is located at a distance of about two meters from the copper bar and has a two degree lateral movement and inclination.

12. A method of counting and determining the size of cracks and bubbles, through a non-contact device based on the digitalization of images, that measures and counts in real time the surface flaws on a metal bar, wherein the said metal bar is a copper bar comprising the steps of:
  a) heating a surface area of the copper bar in the absence of external illumination
  b) sprinkling the heated area with a flow of low pressurized water to cool the outer surface area of the copper bar to form a contrasted surface; said contrasted surface comprising a light and dark area;
  c) imaging the contrasted area with a video camera to produce image data; and
  d) analyzing the image data with a personal computer to count the number and size of cracks and bubbles on said surface.

13. The method of claim 12 wherein the imaging step further comprises utilizing a CCD sensitive element.

14. The method of claim 12 wherein the analyzing step further comprises counting the number of and sizing the dark areas.

15. A method of counting and determining the size of cracks and bubbles, through a non-contact device based on the digitalization of images, that measures and counts in real time the surface flaws on a metal bar, wherein the said metal bar is a copper bar, comprising the steps of a) heating the copper bar;
b) cooling the outer surface area of the heated bar with low pressurized water;
c) imaging the cooled bar to produce image data;
d) analyzing the image data for differences in color intensity level of the image to determine the presence of imperfections.

16. The method of claim 15 wherein the cooling step comprises sprinkling the heated bar with pressurized water to form contrasted surface, said contrasted surface comprising a light and dark area.

17. The method of claim 15 wherein the imaging step further comprises utilizing a CCD sensitive element.

18. The method according to claim 15 wherein the analyzing step further comprises identifying a black color as an imperfection.

19. The method according to claim 18 wherein the analyzing step further comprises counting the number of and sizing the black color.

20. The method of claim 16 wherein the contrasted surface is optimized by establishing a temperature difference between vapor caught in the bubbles and the bar metal through the flow of water.

* * * * *